United States Patent
Nukui

(10) Patent No.: US 6,359,955 B1
(45) Date of Patent: Mar. 19, 2002

(54) TWIN ASYMMETRIC SCAN SLICE THICKNESS SETTING METHOD AND APPARATUS AND RADIATION TOMOGRAPHY METHOD AND APPARATUS

(75) Inventor: Masatake Nukui, Tokyo (JP)

(73) Assignee: GE Yokogawa Medical Systems, Limited, Tokyo (JP)

( * ) Notice: Subject to any disclaimer, the term of this patent is extended or adjusted under 35 U.S.C. 154(b) by 0 days.

(21) Appl. No.: 09/543,070

(22) Filed: Apr. 5, 2000

(30) Foreign Application Priority Data

Jun. 4, 1999 (JP) .......................................... 11-158717

(51) Int. Cl.$^7$ ................................................ A61B 6/00
(52) U.S. Cl. ............................................ 378/4; 378/19
(58) Field of Search ................................ 378/4, 19, 20, 378/11

(56) References Cited

U.S. PATENT DOCUMENTS

| 5,228,069 A | 7/1993 | Arenson |
| 5,430,784 A | 7/1995 | Ribner |
| 5,570,403 A | 10/1996 | Yamazaki |
| 5,848,117 A | * 12/1998 | Urchuk et al. ................. 378/19 |
| 5,946,371 A | * 8/1999 | Lai .............................. 378/19 |
| 6,023,494 A | 2/2000 | Senzig et al. |
| 6,137,858 A | 10/2000 | Horiuchi |

FOREIGN PATENT DOCUMENTS

| DE | 19748891 | 6/1998 |
| EP | 0985379 | 3/2000 |

* cited by examiner

Primary Examiner—David V. Bruce
Assistant Examiner—Pamela R. Hobden
(74) Attorney, Agent, or Firm—Moonray Kojima

(57) ABSTRACT

In order to allow slice thicknesses to be set for a twin asymmetric scan in which a scan is performed with a first slice thickness in a first detector row of a multi detector and with a second slice thickness different than the first slice thickness in a second detector row, first, a position of an X-ray beam is moved and a scan is performed while keeping the width of the X-ray beam fixed at twice the first slice thickness to move the position of the X-ray beam to a position at which count values for the first and second detector rows match (ST2–ST5). The count value for the detector row at this time is stored (ST6). Next, the position of the X-ray beam is moved and a scan is performed while keeping the width of the X-ray beam fixed at the sum of the first and second slice thicknesses to move the position of the X-ray beam to a position at which the count value for the first detector row matches the stored count value (ST7–ST9).

16 Claims, 4 Drawing Sheets

TWIN ASYMMETRIC SCAN SLICE THICKNESS SETTING METHOD AND APPARATUS AND RADIATION TOMOGRAPHY METHOD AND APPARATUS

BACKGROUND OF THE INVENTION

The present invention relates to a twin asymmetric scan slice thickness setting method and apparatus and a radiation tomography method and apparatus, and more particularly to a method of setting slice thicknesses for a twin asymmetric scan in which a scan is performed with a first slice thickness in a first detector row of a multi detector and with a second slice thickness different than the first slice thickness in a second detector row, and an apparatus which can suitably implement the method.

In a conventional X-ray CT apparatus comprising a twin detector having first and second detector rows, a slice thickness setting method is known for a twin symmetric scan in which a scan is performed with the same slice thickness in both the first and second detector rows.

The slice thickness setting method for the twin symmetric scan involves moving a position of an X-ray beam and performing a scan while keeping the width of the X-ray beam fixed at twice the slice thickness to move the position of the X-ray beam to a position at which count values for the first and second detector rows match.

However, a slice thickness setting method for a twin asymmetric scan in which a scan is performed with a first slice thickness in a first detector row and with a second slice thickness different than the first slice thickness in a second detector row is not known in the prior art.

SUMMARY OF THE INVENTION

It is an object of the present invention to provide a twin asymmetric scan slice thickness setting method and apparatus for setting slice thicknesses for the aforementioned twin asymmetric scan, and a radiation tomography method and apparatus which can suitably implement the method.

In accordance with a first aspect of the present invention, there is provided a twin asymmetric scan slice thickness setting method for performing a scan with a first slice thickness in a first detector row of a multi detector and with a second slice thickness different than the first slice thickness in a second detector row, comprising the steps of moving a position of a penetrating radiation beam and performing a scan while keeping the width of the penetrating radiation beam fixed at twice the first slice thickness to move the position of the penetrating radiation beam to a position at which count values for the first and second detector rows match, storing the count value for the detector row at this time, and then moving the position of the penetrating radiation beam and performing a scan while keeping the width of the penetrating radiation beam fixed at the sum of the first and second slice thicknesses to move the position of the penetrating radiation beam to a position at which the count value for the first detector row matches the stored count value.

The sensitivity profile of each of the first and second detector rows in the slice thickness direction has an inverse U-like shape having the crest in the center, gradually falling toward the ends (see FIG. 1(b)). Hence, a relation (first slice thickness:second slice thickness)=(count value for the first detector row:count value for the second detector row) does not stand. That is, the ratio between the count values cannot determine the position of the penetrating radiation beam when the first slice thickness the second slice thickness.

However, since the sensitivity profiles of the first and second detector rows in the slice thickness direction can be considered to be symmetric as viewed from the boundary between the first and second detector rows, a relation (count value for the first detector row count value for the second detector row) stands when the first slice thickness=the second slice thickness. That is, the position of the penetrating radiation beam can be determined by the ratio between the count values (1:1) when the first slice thickness=the second slice thickness.

The present invention utilizes the above-described principle.

More specifically, according to the twin asymmetric scan slice thickness setting method of the first aspect, first, a position of the penetrating radiation beam is moved and a scan is performed while keeping the width of the penetrating radiation beam fixed at twice the first slice thickness to move the position of the penetrating radiation beam to a position at which count values for the first and second detector rows match (i.e., to a position at which the ratio of the count values is 1:1). At this time, the slice thickness in the first detector row and the slice thickness in the second detector row are equal to the first slice thickness. Then, the count value f or the detector rows at this time is stored. Next, the position of the penetrating radiation beam is moved and a scan is performed while keeping the width of the penetrating radiation beam fixed at the sum of the first and second slice thicknesses to move the position of the penetrating radiation beam to a position at which the count value for the first detector row matches the stored count value. At this time, the slice thickness in the first detector row is equal to the first slice thickness. On the other hand, since the slice thickness in the second detector row has a value subtracting the first slice thickness from the sum of the first and second slice thicknesses, the slice thickness in the second detector row is equal to the second slice thickness. The slice thicknesses can thus be set for a twin asymmetric scan.

In accordance with a second aspect of the present invention, there is provided a twin asymmetric scan slice thickness setting method for performing a scan with a first slice thickness in a first detector row of a multi detector and with a second slice thickness different than the first slice thickness in a second detector row, comprising the steps of: moving a position of a penetrating radiation beam and performing a scan while keeping the width of the penetrating radiation beam fixed at twice the first slice thickness to move the position of the penetrating radiation beam to a position at which count values for the first and second detector rows match, storing the count value for the detector row at this time, and then moving the position of the penetrating radiation beam and performing a scan while keeping the width of the penetrating radiation beam fixed at the sum of the first and second slice thicknesses to move the position of the penetrating radiation beam to a position at which the count value for the first detector row matches the stored count value, storing a ratio a between the count values for the first and second detector rows at this time; prior to performing an actual scan of a subject, acquiring a count value for a first control detector disposed corresponding to the first detector row and a count value for a second control detector disposed corresponding to the second detector row, and moving a position of the penetrating radiation beam to a position at which a ratio β between these count values matches the stored ratio α.

According to the twin asymmetric scan slice thickness setting method of the second aspect, the slice thicknesses are set for a twin asymmetric scan based on the twin asymmetric scan slice thickness setting method as described regarding the first aspect. Then, a ratio a between the count values for the first and second detector rows at this time is stored. Thereafter, and prior to performing an actual scan of a subject, a count value for a first control detector disposed corresponding to the first detector row and a count value for a second control detector disposed corresponding to the second detector row are acquired, and the position of the penetrating radiation beam is moved to a position at which a ratio β between these count values matches the stored ratio α. Thus, if the reference ratio α is obtained by performing the twin asymmetric scan slice thickness setting method of the first aspect only once, the ratio can be used as many times as desired in the subsequent actual scans, thereby simplifying the operations for setting the slice thicknesses for an asymmetric scan as a whole.

In accordance with a third aspect of the present invention, there is provided a radiation tomography apparatus comprising a multi detector having a first detector row having a first slice thickness and a second detector row having a second slice thickness, comprising means for acquiring a count value corresponding to the first slice thickness, for moving a position of a penetrating radiation beam and performing a scan while keeping the width of the penetrating radiation beam fixed at twice the first slice thickness to move the position of the penetrating radiation beam to a position at which count values for the first and second detector rows match, storing the count value for the detector row at this time; and means for setting a position of the penetrating radiation beam, for moving the position of the penetrating radiation beam and performing a scan while keeping the width of the penetrating radiation beam fixed at the sum of the first and second slice thicknesses to move the position of the penetrating radiation beam to a position at which the count value for the first detector row matches the stored count value.

The radiation tomography apparatus of the third aspect can suitably implement the twin asymmetric scan slice thickness setting method as described regarding the first aspect.

In accordance with a fourth aspect of the present invention, there is provided a radiation tomography apparatus comprising a multi detector having first and second detector rows, comprising means for storing a reference ratio, for storing a ratio α between a count value for the first detector row having a first slice thickness and a count value for the second detector row having a second slice thickness different than the first slice thickness; and means for setting a position of a penetrating radiation beam, for, prior to performing an actual scan of a subject, acquiring a count value for a first control detector disposed corresponding to the first detector row and a count value for a second control detector disposed corresponding to the second detector row, and moving a position of the penetrating radiation beam to a position at which a ratio β between these count values matches the stored ratio α.

According to the radiation tomography apparatus of the fourth aspect, a ratio α between the count values for the first and second detector rows is stored when the slice thicknesses are set for a twin asymmetric scan based on the twin asymmetric scan slice thickness setting method as described regarding the first aspect, and the ratio is used in an actual scan to set the slice thicknesses for the asymmetric scan. Thus, the stored ratio α can be used as many times as desired in the subsequent actual scans, thereby simplifying the operations for setting the slice thicknesses for an asymmetric scan as a whole.

Therefore, according to the twin asymmetric scan slice thickness setting method and apparatus and a radiation tomography method and apparatus of the present invention, slice thicknesses can be set for a twin asymmetric scan in which a scan is performed with a first slice thickness in a first detector row of a multi detector and with a second slice thickness different than the first slice thickness in a second detector row.

Further objects and advantages of the present invention will be apparent from the following description of the preferred embodiments of the invention as illustrated in the accompanying drawings.

DETAILED DESCRIPTION OF THE INVENTION

The present invention will now be described in more detail with reference to several embodiments shown in the accompanying drawings.

Figure 2:
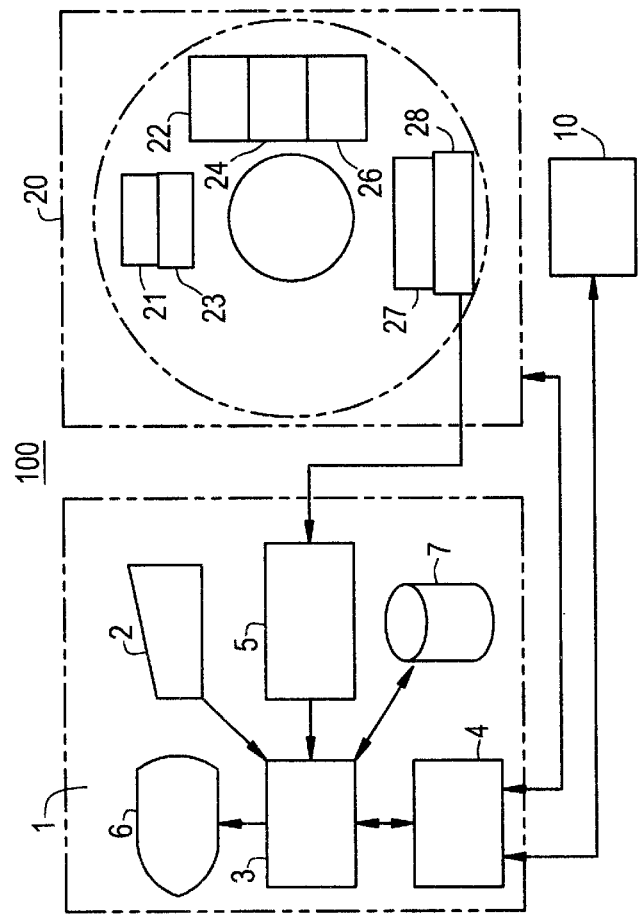
FIG. 2 is a block diagram of an X-ray CT apparatus in accordance with an embodiment of the present invention.

FIG. 2 is a block diagram of an X-ray CT apparatus 100 which is an example of a radiation tomography apparatus in accordance with an embodiment of the present invention.

The X-ray CT apparatus 100 comprises an operating console 1, an imaging table 10 and a scan gantry 20.

The operating console 1 comprises an input device 2 for accepting a command or information input supplied by a human operator, a central processing apparatus 3 for executing a twin asymmetric scan slice thickness setting process, an actual scan process and an image reconstructing process, a control interface 4 for exchanging a control signal and the like with the imaging table 10 and the scan gantry 20, a data collecting buffer 5 for collecting data acquired at the scan gantry 20, a CRT 6 for displaying an X-ray image reconstructed from the data, and a storage device 7 for storing a program, data and an X-ray image.

The scan gantry 20 comprises an X-ray tube 21, an X-ray controller 22, a collimator 23, a collimator controller 24, a rotation controller 26 for rotating the X-ray tube 21 and the like around an iso-center (designated as IC in FIG. 3), and a twin detector 27 having two detector rows.

Figure 3:
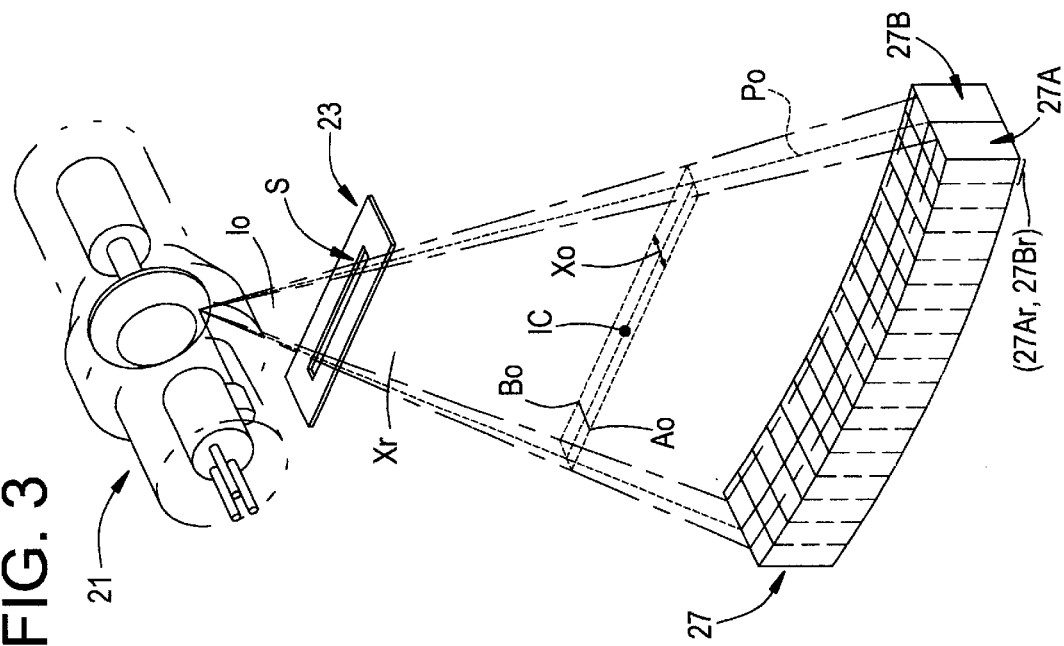
FIG. 3 is a schematic view showing an X-ray tube, a collimator and a twin detector.

FIG. 3 is a schematic view showing the X-ray tube 21, the collimator 23 and the twin detector 27.

An X-ray lo emitted from the X-ray tube 21 is formed into a flat X-ray beam Xr after passing through an aperture S of the collimator 23, and impinges upon a first detector row 27A and a second detector row 27B of the twin detector 27.

The opening width and position of the aperture S of the collimator 23 is regulated by the collimator controller 24 based on a command from the central processing apparatus 3.

An imaginary boundary Po is an imaginary line indicating the boundary between a portion of the X-ray beam Xr that impinges upon the first detector row 27A and a portion that impinges upon the second detector row 27B.

The width of the X-ray beam Xr at the iso-center IC is referred to as an X-ray beam width Xo. The width of a portion of the X-ray beam width Xo that impinges upon the first detector row 27A is designated as a first slice thickness Ao and the width of a portion that impinges upon the second detector row 27B is designated as a second slice thickness Bo.

It should be noted that a detector at the end of the first detector row 27A is defined as a first control detector 27Ar, and a detector at the end of the second detector row 27B is defined as a second control detector 27Br.

Figure 4:
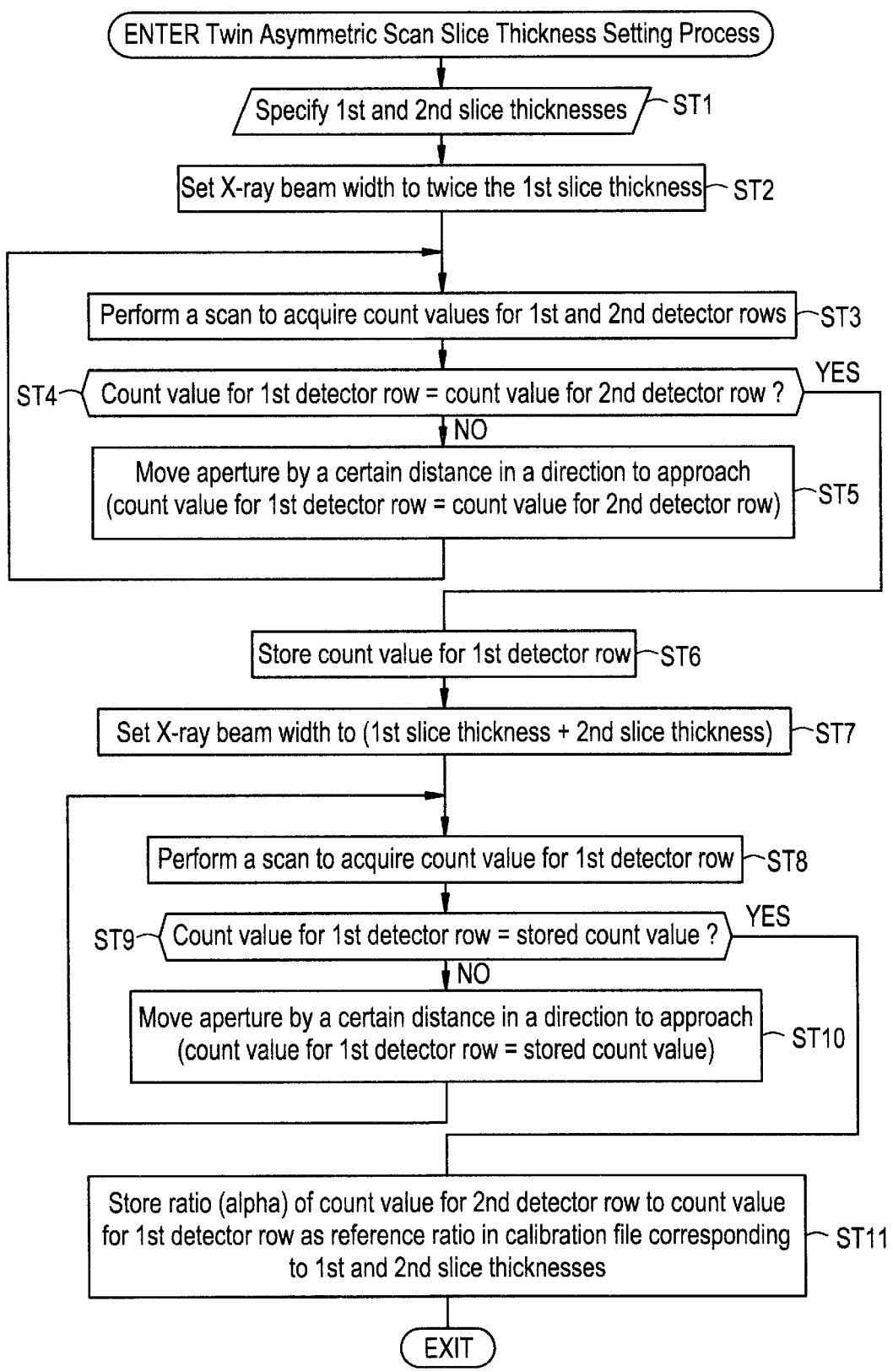
FIG. 4 is a flow chart of a twin asymmetric scan slice thickness setting process.

FIG. 4 is a flow chart of a twin asymmetric scan slice thickness setting process.

In Step ST1, a first slice thickness Ao (e.g., 1 mm) and a second slice thickness Bo (e.g., 9 mm) are specified by the operator as desired using the input device 2.

In Step ST2, the opening width of the aperture S is set so that the X-ray beam width Xo is equal to twice the first slice thickness Ao (e.g., 2 mm).

In Step ST3, a scan is performed (e.g., in 120 kV-60 mA-1 sec-stationary scan) to obtain a count value for the first detector row 27A and a count value for the second detector row 27B.

In Step ST4, the count value for the first detector row 27A and the count value for the second detector row 27B are compared, and if the count values are not equal the process goes to Step ST5; otherwise to Step ST6.

In Step ST5, the aperture S is moved by a certain distance in a direction to approach the condition (count value for the first detector row 27A=count value for the second detector row 27B). Then, the process goes back to Step ST3.

In Step ST6, the count value for the first detector row 27A is stored.

Figure 1A:
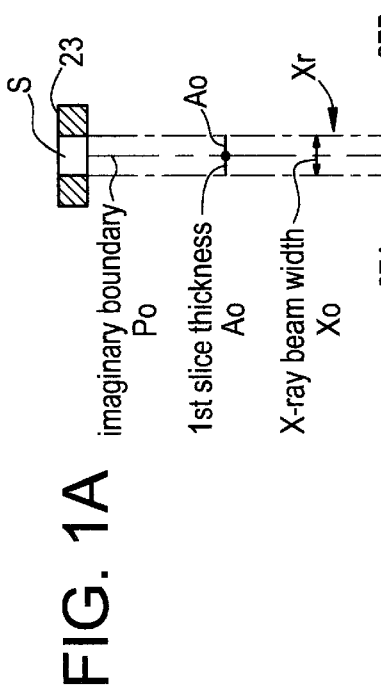
FIG. 1 illustrates a condition in which an X-ray beam is positioned so that first and second detector rows have the same first slice thickness.
Figure 1B:
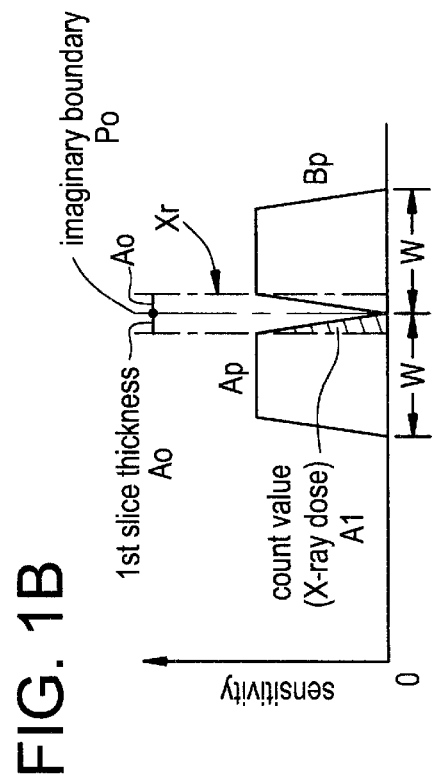

The position relationship among the first detector row 27A, the second detector row 27B and the X-ray beam Xr at this time is shown in FIG. 1(*a*).

The width of each of the first and second detector rows 27A and 27B is designed as W (e.g., 17 mm).

FIG. 1(*b*) shows a sensitivity profile Ap of the first detector row 27A, a sensitivity profile Bp of the second detector row 27B and a count value A1 for the first detector row 27A. The count value A1 can be indicated by the area of the intersection (illustrated as a hatched area) of the sensitivity profile Ap of the first detector row 27A with the X-ray beam Xr.

In Step ST7, the opening width of the aperture S is set so that the X-ray beam width Xo is equal to the first slice thickness Ao+the second slice thickness Bo (e.g., 1+9=10 mm).

In Step ST8, a scan is performed (e.g., in 120 kV-60 mA-1 sec-stationary scan) to obtain a count value for the first detector row 27A.

In Step ST9, the count value for the first detector row 27A and the stored count value are compared, and if the count values are not equal the process goes to Step ST10; otherwise to Step ST11.

In Step ST10, the aperture S is moved by a certain distance in a direction to approach the condition (count value for the first detector row 27A=stored count value). Then the process goes back to Step ST8.

In Step ST11, a ratio $\alpha$ of the count value for the second detector row 27B to the count value for the first detector row 27A is stored in a calibration file as a reference ratio corresponding to the first and second slice thicknesses Ao and Bo. Then, the process is terminated.

Figure 5A:
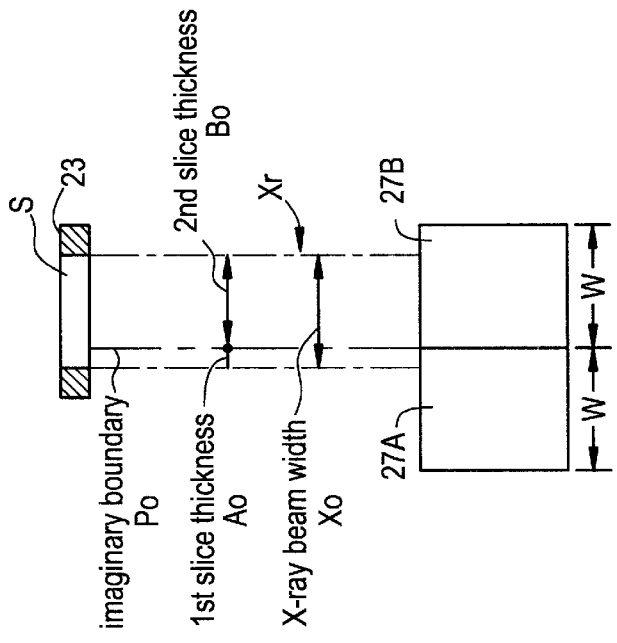
FIG. 5 illustrates a condition in which the X-ray beam is positioned so that the first detector row has α first slice thickness and the second detector row has a second slice thickness.
Figure 5B:
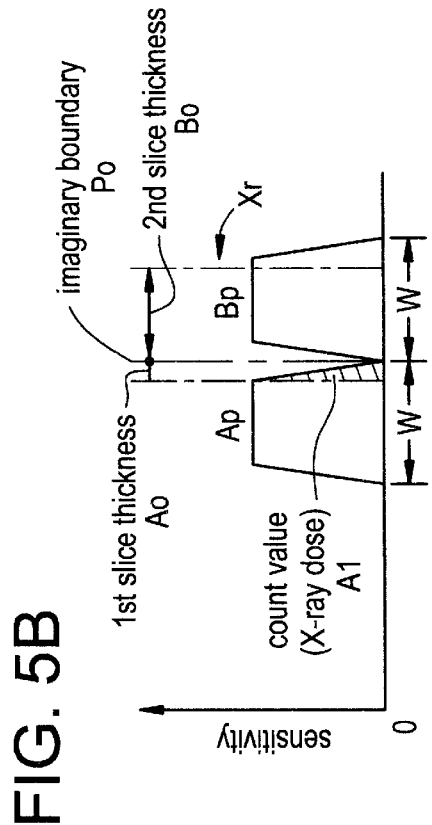

The position relationship among the first detector row 27A, the second detector row 27B and the X-ray beam Xr at the time of the termination is shown in FIG. 5(*a*).

FIG. 5(*b*) shows a sensitivity profile Ap of the first detector row 27A, a sensitivity profile Bp of the second detector row 27B and a count value A1 for the first detector row 27A.

Figure 6:
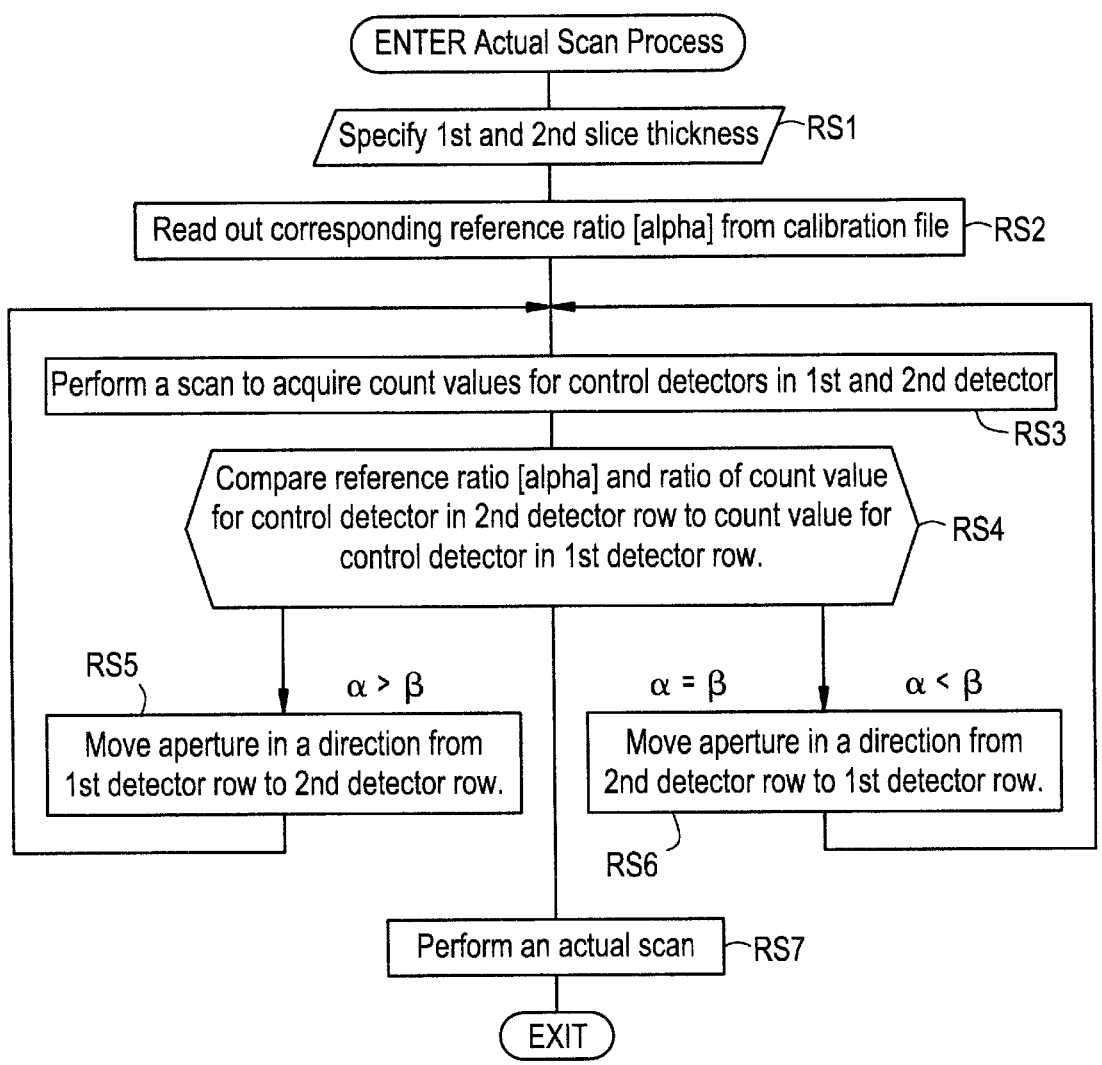
FIG. 6 is a flow chart of an actual scan process.

FIG. 6 is a flow chart of an actual scan process.

In Step RS1, a first slice thickness Ao and a second slice thickness Bo are specified by the operator as desired using the input device 2.

In Step RS2, the reference ratio $\alpha$ is read out, which has been stored in the calibration file corresponding to the first and second slice thicknesses Ao and Bo.

In Step RS3, a scan is performed (e.g., in 120 kV-60 mA-1 sec-stationary scan) to obtain a count value for the first detector row 27A.

In Step RS4, a count value for the first control detector 27Ar and a count value for the second control detector 27Br are obtained and a ratio $\beta$ of the latter count value to the former one is compared with the reference value $\alpha$. If $\alpha>\beta$ the process goes to Step RS5; if $\alpha<\beta$ the process goes to Step RS6; and if $\alpha=\beta$ the process goes to Step RS7.

In Step RS5, the aperture S is moved by a certain distance in a direction from the first detector row 27A to the second detector row 27B. Then, the process goes back to Step RS3.

In Step RS6, the aperture S is moved by a certain distance in a direction from the second detector row 27B to the first detector row 27A. Then, the process goes back to Step RS3.

In Step RS7, an actual scan of the subject is performed with the first slice thickness Ao set for the first detector row 27A and with the second slice thickness Bo set for the second detector row 27B. Then, the process is terminated.

According to the X-ray CT apparatus 100 as above, a first slice thickness Ao and a second slice thickness Bo different than the first slice thickness Ao can be set in the first detector row 27A and the second detector row 27B of the twin detector 27.

Many widely different embodiments of the invention may be configured without departing from the spirit and the scope of the present invention. It should be understood that the present invention is not limited to the specific embodiments described in the specification, except as defined in the appended claims.

What is claimed is:

1. A twin asymmetric scan slice thickness setting method for performing a scan with a first slice thickness in a first detector row of a multi detector and with a second slice thickness different than said first slice thickness in a second detector row, comprising the steps of:

moving a position of a penetrating radiation beam and performing a scan while keeping the width of the penetrating radiation beam fixed at twice said first slice thickness to move the position of the penetrating radiation beam to a position at which count values for said first and second detector rows match, storing the count value for the detector row at this time, and then moving the position of the penetrating radiation beam and performing a scan while keeping the width of the penetrating radiation beam fixed at the sum of said first and second slice thicknesses to move the position of the penetrating radiation beam to a position at which the count value for said first detector row matches said stored count value.

2. The twin asymmetric scan slice thickness setting method as defined in claim 1, wherein an X-ray is employed as said radiation.

3. A twin asymmetric scan slice thickness setting apparatus employing a multi detector having a first detector row having a first slice thickness and a second detector row having a second slice thickness, comprising:

means for acquiring a count value corresponding to the first slice thickness, for moving a position of a penetrating radiation beam and performing a scan while keeping the width of the penetrating radiation beam fixed at twice said first slice thickness to move the position of the penetrating radiation beam to a position at which count values for said first and second detector rows match, storing the count value for the detector row at this time; and means for setting a position of the penetrating radiation beam, for moving the position of the penetrating radiation beam and performing a scan while keeping the width of the penetrating radiation beam fixed at the sum of said first and second slice thicknesses to move the position of the penetrating radiation beam to a position at which the count value for said first detector row matches said stored count value.

4. The twin asymmetric scan slice thickness setting apparatus as defined in claim 3, wherein an X-ray is employed as said radiation.

5. A twin asymmetric scan slice thickness setting method for performing a scan with a first slice thickness in a first detector row of a multi detector and with a second slice thickness different than said first slice thickness in a second detector row, comprising the steps of:

moving a position of a penetrating radiation beam and performing a scan while keeping the width of the penetrating radiation beam fixed at twice said first slice thickness to move the position of the penetrating radiation beam to a position at which count values for said first and second detector rows match, storing the count value for the detector row at this time, and then moving the position of the penetrating radiation beam and performing a scan while keeping the width of the penetrating radiation beam fixed at the sum of said first and second slice thicknesses to move the position of the penetrating radiation beam to a position at which the count value for said first detector row matches said stored count value, storing a ratio α between the count values for said first and second detector rows at this time; and prior to performing an actual scan of a subject, acquiring a count value for a first control detector disposed corresponding to said first detector row and a count value for a second control detector disposed corresponding to said second detector row, and moving a position of the penetrating radiation beam to a position at which a ratio β between these count values matches said stored ratio α.

6. The twin asymmetric scan slice thickness setting method as defined in claim 5, wherein an X-ray is employed as said radiation.

7. A twin asymmetric scan slice thickness setting apparatus employing a multi detector having first and second detector rows, comprising:

means for storing a reference ratio, for storing a ratio α between a count value for said first detector row having a first slice thickness and a count value for said second detector row having a second slice thickness different than said first slice thickness; and means for setting a position of a penetrating radiation beam, for, prior to performing an actual scan of a subject, acquiring a count value for a first control detector disposed corresponding to said first detector row and a count value for a second control detector disposed corresponding to said second detector row, and moving a position of the penetrating radiation beam to a position at which a ratio β between these count values matches said stored ratio α.

8. The twin asymmetric scan slice thickness setting apparatus as defined in claim 7, wherein an X-ray is employed as said radiation.

9. A radiation tomography apparatus comprising a multi detector having a first detector row having a first slice thickness and a second detector row having a second slice thickness, comprising:

means for acquiring a count value corresponding to a first slice thickness, for moving a position of a penetrating radiation beam and performing a scan while keeping the width of the penetrating radiation beam fixed at twice said first slice thickness to move the position of the penetrating radiation beam to a position at which count values for said first and second detector rows match, storing the count value for the detector row at this time; and means for setting a position of the penetrating radiation beam, for moving the position of the penetrating radiation beam and performing a scan while keeping the width of the penetrating radiation beam fixed at the sum of said first and second slice thicknesses to move the position of the penetrating radiation beam to a position at which the count value for said first detector row matches said stored count value.

10. The radiation tomography apparatus as defined in claim 9, wherein an X-ray is employed as said radiation.

11. A radiation tomography method for performing a scan with a first slice thickness in a first detector row of a multi detector and with a second slice thickness different than said first slice thickness in a second detector row, comprising the steps of:

moving a position of a penetrating radiation beam and performing a scan while keeping the width of the penetrating radiation beam fixed at twice said first slice thickness to move the position of the penetrating radiation beam to a position at which count values for said first and second detector rows match, storing the count value for the detector row at this time, and then moving the position of the penetrating radiation beam and performing a scan while keeping the width of the penetrating radiation beam fixed at the sum of said first and second slice thicknesses to move the position of the penetrating radiation beam to a position at which the count value for said first detector row matches said stored count value.

12. The radiation tomography method as defined in claim 11, wherein an X-ray is employed as said radiation.

13. A radiation tomography apparatus comprising a multi detector having first and second detector rows, comprising:

means for storing a reference ratio, for storing a ratio α between a count value for said first detector row having a first slice thickness and a count value for said second detector row having a second slice thickness different than said first slice thickness; and means for setting a position of a penetrating radiation beam, for, prior to performing an actual scan of a subject, acquiring a count value for a first control detector disposed corresponding to said first detector row and a count value for a second control detector disposed corresponding to said second detector row, and moving a position of the penetrating radiation beam to a position at which a ratio $\beta$ between these count values matches said stored ratio $\alpha$.

14. The radiation tomography apparatus as defined in claim 13, wherein an X-ray is employed as said radiation.

15. A radiation tomography method for performing a scan with a first slice thickness in a first detector row of a multi detector and with a second slice thickness different than said first slice thickness in a second detector row, comprising the steps of:

moving a position of a penetrating radiation beam and performing a scan while keeping the width of the penetrating radiation beam fixed at twice said first slice thickness to move the position of the penetrating radiation beam to a position at which count values for said first and second detector rows match, storing the count value for the detector row at this time, and then moving the position of the penetrating radiation beam and performing a scan while keeping the width of the penetrating radiation beam fixed at the sum of said first and second slice thicknesses to move the position of the penetrating radiation beam to a position at which the count value for said first detector row matches said stored count value, storing a ratio $\alpha$ between the count values for said first and second detector rows at this time; and prior to performing an actual scan of a subject, acquiring a count value for a first control detector disposed corresponding to said first detector row and a count value for a second control detector disposed corresponding to said second detector row, and moving a position of the penetrating radiation beam to a position at which a ratio $\beta$ between these count values matches said stored ratio $\alpha$.

16. The radiation tomography method as defined in claim 15, wherein an X-ray is employed as said radiation.

* * * * *